(12) United States Patent
Bonrath et al.

(10) Patent No.: US 7,135,580 B2
(45) Date of Patent: Nov. 14, 2006

(54) PROCESS FOR THE MANUFACTURE OF α-TOCOPHERYL ACETATE

(75) Inventors: Werner Bonrath, Freiburg (DE); Claus Dittel, Solothurn (CH); Lisa Giraudi, Huningue (FR); Thomas Netscher, Bad Krozingen (DE); Thomas Pabst, Mintraching (DE)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 10/541,360

(22) PCT Filed: Dec. 22, 2003

(86) PCT No.: PCT/EP03/14723

§ 371 (c)(1), (2), (4) Date: Jul. 6, 2005

(87) PCT Pub. No.: WO2004/063182

PCT Pub. Date: Jul. 29, 2004

(65) Prior Publication Data

US 2006/0052618 A1 Mar. 9, 2006

(30) Foreign Application Priority Data

Jan. 13, 2003 (EP) .............................. 03000493
Oct. 23, 2003 (EP) .............................. 0302488

(51) Int. Cl.
*C07D 311/72* (2006.01)
(52) U.S. Cl. .................................. 549/411
(58) Field of Classification Search ............... 549/411
See application file for complete search history.

(56) References Cited

U.S. PATENT DOCUMENTS

| 3,615,169 A | 10/1971 | Thom et al. |
| 6,048,988 A | 4/2000 | Krill et al. |
| 2005/0038269 A1 | 2/2005 | Giraudi et al. |

FOREIGN PATENT DOCUMENTS

| EP | 0 658 552 | 6/1995 |
| EP | 0 850 910 | 7/1998 |
| EP | 0 916 642 | 5/1999 |
| EP | 1 239 045 | 9/2002 |
| WO | WO 96/19288 | 6/1996 |
| WO | WO 98/21197 | 5/1998 |

OTHER PUBLICATIONS

Schneider et al, "Industrial application of Nafion-systems in rearrangement-aromatisation, transesterification, alkylation, and ring-closure reactions", Applied Catalysis A: General, Elsevier Science, Amsterdam, NL, vol. 220, No. 1-2, Oct. 25, 2001, pp. 51-58.
1987 American Chemical Society; "Improved General Method of Ortho Alkylation of Phenols Using Alkyl Isopropyl Sulfide, Sulfuryl Chloride, and Triethylamine. An Expedient Synthesis of Representative Oxygen Heterocycles and (2R, 4'R, 8'R)-α- Tocopherol"; J. Org. Chem. 52, pp. 5495-5497, 1987.
Werner Bonrath et al; "Catalytic Processes in Vitamins Synthesis and Production"; Applied Catalysis A: General 280 (2005), pp. 55-73.
Anthony G.M. Barrett et al; "Synthesis of Some Ytterbium (III) tris-(perfluoroalkylsulfonyl)methides"; Tetrahedron 58 (2002); pp. 3835-3840.
Moulay El Mustapha Hamidi et al; "Synthesis and Structural Characterization of Some Anhydrous Ln(OTf)$_3$ Complexes (Ln=Sc, La, Nd, Sm, Gd and Er; OTf=CF$_3$SO$_3$)"; Polyhedron vol. 13, No. 11; 1994; pp. 1787-1792.
Mark A. Harmer et al; "High Surface Area Nafion Resin/Silica Nanocomposites: A New Class of Solid Acid Catalyst"; J. Am. Chem. Soc. 1996, 118; pp. 7708-7715.
Shu Kobayashi et al; "Scandium Perfluoroalkanesulfonate-Catalyzed Diels—Alder Reactions in an Organic Solvent"; Journal of Organometallic Chemistry 624 (2001); pp. 392-394.
M. Schneider et al; "Industrial Application of Nafion-Systems in Rearrangement-Aromatisation, Trasesterification, Alkylation, and Ring-Closure Reactions"; Applied Catalysis A: General 220 (2001); pp. 51-58.

*Primary Examiner*—Taofiq Solola
(74) *Attorney, Agent, or Firm*—Nixon & Vanderhye P.C.

(57) ABSTRACT

The present invention is concerned with a novel process for the manufacture of α-tocopheryl acetate which comprises reacting 2,3,6-trimethylhydroquinone-1-acetate with a compound selected from the group consisting of phytol (formula IV with R=OH), iso-phytol (formula III with R=OH), and (iso) phytol derivatives represented by the following formulae III and IV with R=$C_2$-to $C_5$-alkonoyloxy, benzoyloxy, mesyloxy, bezenesul-fonyloxy or tosyloxy,

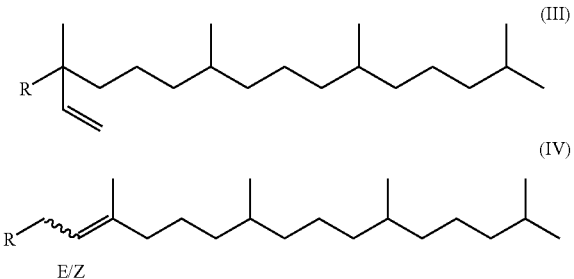

(IV) in the presence of a catalyst of the formula $M^{n+}(R^1SO_3^-)_n$, wherein $M^{n+}$ is a silver, copper, gallium, hafnium or rare earth metal cation, n is the valence of the cation $M^{n+}$, and $R_1$ is fluorine, $C_{1-8}$-perfluoroalkyl or perfluoroaryl, and, if required, cyclizing any 3-phytyl-2,5,6-trimethylhydroquinone-1-acetate or a double bond isomer thereof obtained as an intermediate reaction product, to produce α-tocopheryl acetate. In the catalyst $M^{n+}$ is preferably $Ag^+$, $Cu^+$, $Ga^{3+}$, $Sc^{3+}$, $Lu^{3+}$, $Ho^{3+}$, $Tm^{3+}$, $Yb^{3+}$ or $Hf^{4+}$.

16 Claims, No Drawings

PROCESS FOR THE MANUFACTURE OF α-TOCOPHERYL ACETATE

This application is the US national phase of international application PCT/EP2003/014723 filed 22 Dec. 2003 which designated the U.S. and claims benefit of EP 03000493.1, dated 13 Jan. 2003 and EP 03024288.7, dated 23 Oct. 2003, the entire content of which is hereby incorporated by reference.

The present invention relates to a novel process for the manufacture of α-tocopheryl acetate.

Industrial syntheses of vitamin E, α-tocopherol, are based on the reaction of 2,3,5-tri-methylhydroquinone (TMHQ) with (iso)phytol or phytyl halides, see e.g. Ullmann's Encyclopedia of Industrial Chemistry Vol. A27, VCH (1996), pp. 478–488. TMHQ may be obtained from ketoisophorone via 2,3,5-trimethylhydroquinone diacetate, e.g. as described in EP-A 0 850 910, EP-A 0 916 642, EP-A 0 952 137 or EP-A 1 028 103, and saponification of the latter.

EP-A 0 658 552 also discloses a process for the manufacture of α-tocopherol and derivatives thereof, wherein fluorosulfonates [M(RSO$_3$)$_3$], nitrates [M(NO$_3$)$_3$] and sulfates [M$_2$(SO$_4$)$_3$] are used as the catalysts with M representing a Sc, Y or lanthanide atom, and R representing fluorine, a fluorinated lower alkyl group or an aryl group which may be substituted by one or more fluorine atoms. The reaction is carried out in a solvent which is inert to the catalyst and the starting materials, TMHQ and allyl alcohol derivatives or alkenyl alcohols such as phytol or isophytol, examples of the solvent being aliphatic hydrocarbons, aromatic hydrocarbons and aliphatic esters. Preferably the allyl alcohol derivatives or alkenyl alcohols are used in a molar excess of 4% or 10% compared to TMHQ.

Since α-tocopherol is labile under oxidative conditions, it is usually converted into its acetate which is more stable and more convenient to handle. Thus, the manufacture of the usual commercial form of vitamin E, viz. α-tocopheryl acetate, involves the additional step of esterifying α-tocopherol (as obtained by the reaction of TMHQ with (iso) phytol or phytyl halides).

An example of the latter is the process described in DE-OS 2 160 103, wherein (iso)phytol or a phytyl halide is reacted with TMHQ or 2,3,6-trimethylhydroquinone-1-acetate in the presence of iron or ferrous chloride and hydrogen chloride. In all cases α-tocopherol is obtained which must be converted to its acetate in a further step. The same applies when solid acid catalysts like those disclosed in DE-OS 24 04 621 are used. Even if 2,3,6-tri-methylhydroquinone-1,4-diacetate is used as the starting material, as in the process according to DE-A 100 11 402, α-tocopherol is obtained in a significant amount, so that a further partial acetylation is necessary, because α-tocopherol and α-tocopheryl acetate cannot be easily separated by distillation.

Therefore, the object of the present invention is to provide a process for the manufacture of α-tocopheryl acetate starting from 2,3,6-trimethylhydroquinone-1-acetate in the presence of a catalyst, where a further step of acetylation is avoided.

The object is achieved by a new approach to the manufacture of α-tocopheryl acetate (TCPA). According to this approach, 2,3,6-trimethylhydroquinone-1-acetate (TMHQA) is reacted with either phytol (PH), isophytol (IP) or an (iso)phytol derivative to produce TCPA or 3-phytyl-2,5,6-trimethylhydroquinone-1-acetate (PTMHQA), whereupon the latter is submitted to ring closure to obtain TCPA.

Thus, in a first aspect, the present invention relates to a process which comprises reacting TMHQA represented by the formula II

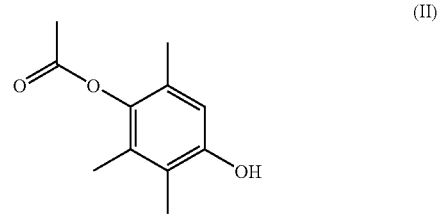

with a compound selected from the group consisting of phytol (formula IV with R=OH), isophytol (formula III with R=OH), and (iso)phytol derivatives represented by the following formulae III and IV with R=C$_{2-5}$-alkanoyloxy, benzoyloxy, methanesulfonyloxy (=mesyloxy), benzenesulfonyloxy or toluenesulfonyloxy (=tosyloxy), preferably selected from the group consisting of phytol, isophytol and (iso)phytol derivatives represented by the following formulae III and IV with R=acetyloxy or benzoyloxy, more preferably selected from the group consisting of phytol and isophytol, most preferably with isophytol,

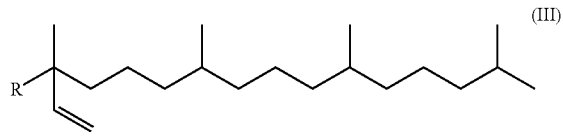

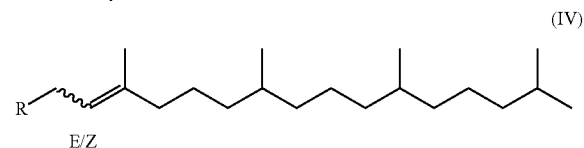

in the presence of a catalyst of the formula M$^{n+}$(R$^1$SO$_3^-$)$_n$, wherein M$^{n+}$ is a silver, copper, gallium, hafnium or rare earth metal cation, n is the valence of the cation M$^{n+}$, and R$^1$ is fluorine, C$_{1-8}$-perfluoroalkyl or perfluoroaryl, to obtain α-tocopheryl acetate represented by the following formula I.

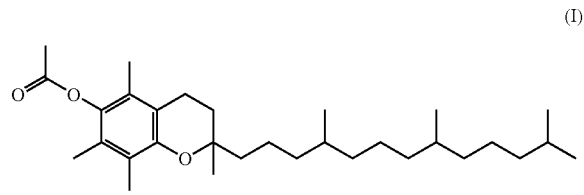

In another aspect, the invention relates to a process which comprises reacting TMHQA with a compound selected from the group consisting of phytol, isophytol, and (iso)phytol derivatives represented by the formulae III and IV, as defined above and with the same preferences, in the presence of a catalyst of the formula M$^{n+}$(R$^1$SO$_3^-$)$_n$, wherein M$^{n+}$, n and R$^1$ are as defined above, to produce 3-phytyl-2,5,6-trimethylhydroquinone-1-acetate represented by the formula V

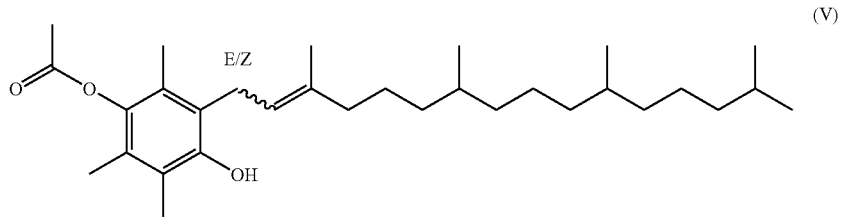

(V)

and/or a double bond isomer thereof and cyclizing the 3-phytyl-2,5,6-trimethylhydroquinone-1-acetate and/or a double bond isomer thereof (as explained below) obtained to produce α-tocopheryl acetate.

Concerning the substituent R: The term "$C_{2-5}$-alkanoyloxy" covers linear $C_{2-5}$-alkanoyloxy and branched $C_{4-5}$-alkanoyloxy. Preferred examples of "$C_{2-5}$-alkanoyloxy" are acetyloxy, propionyloxy and pivaloyloxy.

Concerning the metal cation $M^{n+}$: Examples of rare earth metal cations which may be present in the catalyst for use in the present invention are $Sc^{3+}$, $Y^{3+}$, $Lu^{3+}$, $La^{3+}$, $Ho^{3+}$, $Tm^{3+}$, $Gd^{3+}$ and $Y^{3+}$. Preferred cations are $Ag^+$, $Cu^+$, $Ga^{3+}$, $Sc^{3+}$, $Lu^{3+}$, $Ho^{3+}$, $Tm^{3+}$, $Yb^{3+}$, and $Hf^{4+}$, especially preferred are $Ag^+$, $Ga^{3+}$, $Sc^{3+}$ and $Hf^{4+}$.

Concerning the substituent $R^1$: The term "$C_{1-8}$-perfluoroalkyl" encloses linear $C_{1-8}$-perfluoroalkyl and branched $C_{3-8}$-perfluoroalkyl. Preferably $C_{1-8}$-perfluoroalkyl is trifluoromethyl, pentafluoroethyl or nonafluoro-n-butyl, more preferably trifluoromethyl or nonafluoro-n-butyl, and most preferably trifluoromethyl.

A preferred example for "perfluoroaryl" is perfluorophenyl, which may be single or multiply substituted with trifluoromethyl. A more preferred perfluoroaryl is perfluorophenyl.

The catalysts of the formula $M^{n+}(R^1SO_3^-)_n$ may be obtained e.g. according to the procedures disclosed in U.S. Pat. No. 3,615,169 or in Journal of Organometallic Chemistry 2001, 624, 392–394. The catalyst $Gd(F_3CSO_3)_3$ e.g. can be obtained according to a procedure described by Moulay El Mustapha Hamidi and Jean-Louis Pascal in Polyhedron 1994, 13(11), 1787–1792. $Gd(F_3CSO_3)_3$ is also commercially available from Aldrich (in Buchs, Switzerland), as well as $Sc(F_3CSO_3)_3$, $La(F_3CSO_3)_3$, $Ho(F_3CSO_3)_3$, $Tm(F_3CSO_3)_3$, $Yb(F_3CSO_3)_3$, $F_3CSO_3Ag$, $F_3CSO_3Cu$ benzene complex and $Hf(F_3CSO_3)_4.H_2O$. $Y(F_3CSO_3)_3$ and $Lu(F_3CSO_3)_3$ are commercially available from Fluka (in Buchs, Switzerland). $Ga(F_3CSO_3)_3$ is commercially available from Acros Organics (in Geel, Belgium).

The starting material TMHQA may be obtained e.g. by selective hydrolysis of 2,3,5-trimethylhydroquinone-diacetate as described in EP 1 239 045. The (iso)phytyl compounds can be produced by conventional processes known to the person skilled in the art. Phytol and its derivatives represented by the formulae IV can be used as E/Z-mixture as well as in pure E- or pure Z-form. Preferred is the use of phytol and its derivatives represented by the formulae IV as E/Z-mixtures.

While the manufacture of (all-rac)-α-tocopheryl acetate is preferred the invention is not limited to the manufacture of that particular steric form and other steric forms can be obtained by using phytol, isophytol or a derivative thereof as the starting material in the appropriate isomeric form. Thus, (RS,R,R)-α-tocopheryl acetate will be obtained when using (R,R)-phytol, (R,R,R)-isophytol, or (S,R,R)-isophytol, (RS,R,R)-isophytol or an appropriate (iso)phytol derivative.

In an especially preferred embodiment of the invention TMHQA is reacted with phytol and/or isophytol, more preferably with isophytol, and if required, the intermediate product PTMHQA and/or a double bond isomer thereof cyclized to α-tocopheryl acetate.

The catalyst of the formula $M^{n+}(R^1SO_3^-)_n$, which is stable against protic solvents such as methanol, ethanol and water, can be used in solid form, as well as in solution or in suspension, whereby water or a polar organic solvent such as a cyclic carbonate can be used as the solvent or dispersion medium. The concentration of the catalyst in the solution is not critical. If the reaction is carried out in a biphasic solvent system (see below) the catalyst can be recovered from the polar phase after the reaction. Preferably the catalyst is used in solid form.

Examples of solvents suitable for the reaction of TMHQA with compounds represented by the formulae III and/or IV to PTMHQA (and double bond isomers therof)/TCPA according to the present invention are aprotic non-polar organic solvents such as aliphatic hydrocarbons, aromatic hydrocarbons and mixtures thereof, preferably aliphatic hydrocarbons, as well as aprotic polar solvents such as aliphatic and cyclic carbonates, aliphatic esters and cyclic esters (lactones), aliphatic and cyclic ketones and mixtures thereof.

Preferred examples of aliphatic hydrocarbons are linear, branched or cyclic $C_5$- to $C_{15}$-alkanes. Particularly preferred are linear, branched or cyclic $C_6$- to $C_{10}$-alkanes, especially preferred are hexane, heptane, octane, cyclohexane and methylcyclohexane or mixtures thereof. Preferred examples of aromatic hydrocarbons are benzene, toluene, o-, m- and p-xylene and mixtures thereof. The most preferred non-polar solvent is heptane.

Preferred examples of aliphatic and cyclic carbonates are ethylene carbonate, propylene carbonate and 1,2-butylene carbonate. Preferred examples of aliphatic esters and cyclic esters (lactones) are, ethyl acetate, isopropyl acetate, n-butyl acetate and γ-butyrolactone. Preferred examples of aliphatic and cyclic ketones are diethyl ketone, isobutyl methyl ketone, cyclopentanone and isophorone. Especially preferred are cyclic carbonates and lactones, especially ethylene carbonate, propylene carbonate and γ-butyrolactone. Most preferred are the cyclic carbonates, especially ethylene carbonate and propylene carbonate and mixtures thereof.

More preferred are biphasic solvent systems comprising polar and non-polar solvents.

Examples of non-polar solvents in such biphasic solvent systems are the non-polar solvents named above.

Examples of polar solvents in such biphasic solvent systems are the polar solvents named above.

The most preferred biphasic solvent systems are mixtures of ethylene carbonate and/or propylene carbonate and hexane, heptane or octane, especially mixtures of ethylene carbonate and heptane, mixtures of propylene carbonate and octane, and mixtures of ethylene carbonate, propylene carbonate and heptane.

The molar ratio of TMHQA to a compound represented by formula III and/or IV in the reaction mixture conveniently varies from about 3:1 to about 0.8:1, preferably from about 2:1 to about 1:1, more preferably from about 1.75:1 to about 1:1.

The amount of the catalyst $M^{n+}(R^1SO_3^-)_n$ used is based on the amount of TMHQA or the compound represented by formula III or IV whichever is used in the lesser molar amount. Usually the relative amount of the catalyst of the formula $M^{n+}(R^1SO_3^-)_n$ to the amount of TMHQA or the compound represented by formula III or IV is from about 0.001 to about 1 mol %, preferably from about 0.001 to about 0.1 mol %, more preferably from about 0.003 to about 0.1 mol %. Such catalytic amounts of $M^{n+}(R^1SO_3^-)_n$ are sufficient to obtain high yields of the desired product. In this context the expression "amount of $M^{n+}(R^1SO_3^-)_n$," is to be understood as referring to the weight of pure $M^{n+}(R^1SO_3^-)_n$ present, even though the catalyst may be impure and/or in the form of an adduct with a solvent.

The amount of organic solvent used is conveniently from about 0.25 ml to about 6 ml, preferably from about 0.5 ml to about 3 ml, based on 1 mmol of the compound represented by formula III or IV, whichever is employed, these amounts referring to the total amount of solvent, i.e. regardless of whether the reaction is effected in a single phase (single solvent or a solvent mixture) or in a biphasic solvent system.

If the process is carried out in a biphasic solvent system, then the volume ratio of the non-polar solvent to the polar solvent is conveniently in the range from about 1:5 to about 30:1, preferably from about 1:3 to about 20:1, most preferably about 10:1 to about 15:1

It was found that the cyclic carbonate used in the biphasic solvent systems could be recycled several times.

The alkylation reaction is conveniently carried out at temperatures from about 20° C. to about 160° C., preferably from about 80° C. to about 150° C., more preferably from about 105 to about 150° C., most preferably from about 125 to about 145° C.

The reaction is conveniently carried out at atmospheric pressure.

Moreover, the process is conveniently carried out under an inert gas atmosphere, preferably gaseous nitrogen or argon.

The process in accordance with the invention can be carried out batchwise or continuously, and in general operationally in a very simple manner, for example (1) by adding the compound represented by formula III or IV—as such or dissolved in the non-polar solvent (if the reaction is carried out in a non-polar solvent or a biphasic solvent system) such as mentioned above, preferably as such—portionwise or continuously to a mixture of the catalyst of the formula $M^{n+}(R^1SO_3^-)_n$, TMHQA and the solvent/biphasic solvent system.

It is also possible (2) to add subsequently the catalyst, preferably as such, and the compound represented by the formula III or IV—as such or dissolved in the non-polar solvent (if the reaction is carried out in a non-polar solvent or a biphasic solvent system) such as mentioned above, preferably as such—to TMHQA and the solvent/biphasic solvent system.

The rate of addition of one component to the others is not critical. Conveniently, the compound represented by formula III or IV is added continuously in a rate from about 0.2 to about 1 ml per minute, preferably from about 0.4 to about 0.8 ml per minute. The catalyst is preferably added at once to the mixture of TMHQA and the solvent/biphasic solvent system having already reached the reaction temperature.

After completion of the addition of the compound represented by formula III or IV (in the non-polar solvent) the reaction mixture is suitably heated at the reaction temperature for a further about 10 to about 60 minutes, preferably about 20 to about 30 minutes. The working-up can be effected by procedures conventionally used in organic chemistry.

The conversion of TMHQA to TCPA by the process of this invention may proceed in one step or may be carried out with isolation of an intermediate, PTMHQA. Further, isomers of the latter, viz., (Z)- or (E)-acetic acid 4-hydroxy-2,5,6-trimethyl-3-(3,7,11,15-tetramethyl-hexadec-3-enyl)-phenyl ester (formula VIa) and/or acetic acid 4-hydroxy-2,5,6-trimethyl-3-[3-(4,8,12-trimethyl-tridecyl)-but-3-enyl] phenyl ester (formula VIb) may be formed in minor amounts in the reaction mixture.

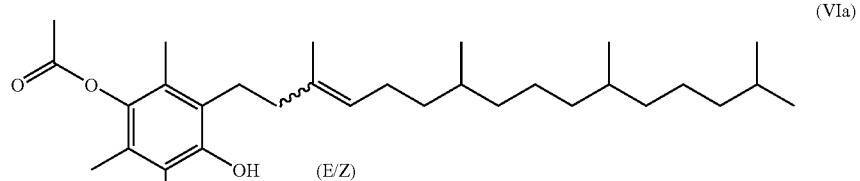

(VIa)

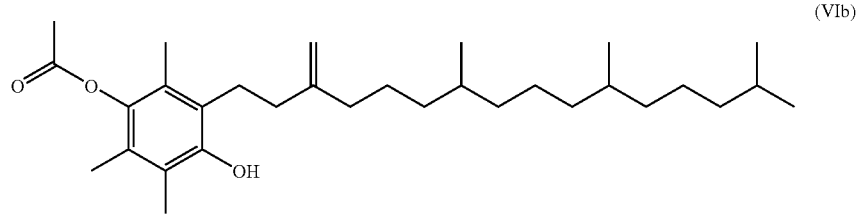

(VIb)

All these intermediates may be cyclized by heating to yield the desired product, TCPA. The cyclization may be carried out using the same catalysts and reaction conditions as those used in the alkylation.

The present invention provides a highly selective and high-yield manufacture of TCPA.

A further advantage in the use of $M^{n+}(R^1SO_3^-)_n$ as defined above as the catalyst in the process in accordance with the invention is, in addition to high yields of (all-rac)-TCPA and high selectivities as well as the enabled ready isolation of the produced (all-rac)-TCPA from the mixture after reaction, that the formation of α-tocopherol is essentially avoided. "Essentially avoided" in the context of the present invention means that the formation of α-tocopherol is ≦3%, preferably ≦2.5%, more preferably ≦1.5%, based on TMHQA or the compound represented by formula III or IV, whichever is used in the lesser amount.

The following examples illustrate the invention further.

EXAMPLES

In the following examples "OTf" means "triflate", i.e. "$F_3CSO_3$".

Example 1

In a four-necked flask equipped with a stirrer, a water separator, and a reflux condenser, 19.7 g (100 mmol) of TMHQA and 25 ml of the solvent (see table 1) were heated with stirring under argon atmosphere to reflux temperature (oil bath 140–145° C.). After the addition of the catalyst (for the relative amount of catalyst, based on IP, see table 1 below), 36.18 ml (100 mmol) of IP were added at a rate of 0.8 ml per minute. The reaction mixture was heated under reflux for 30 minutes after completion of the addition of IP. The reaction mixture was cooled and evaporated under reduced pressure. A viscous oil was obtained. For the yield of (all-rac)-TCPA, based on IP, see table 1. The also formed PTMHQA can be cyclized to TCPA under controlled reaction conditions by prolonging the reaction time resulting in a better overall-yield of TCPA.

Example 2

In a four-necked flask equipped with a stirrer, a water separator, and a reflux condenser, 19.7 g (100 mmol) of TMHQA and 25 ml of γ-butyrolactone were heated with stirring under argon atmosphere to approximately 110° C. (oil bath 115° C.). After the addition of catalyst (for the relative amount of catalyst, based on IP, see table 2), 36.18 ml (100 mmol) of IP were added at a rate of 0.8 ml per minute. The reaction mixture was heated under reflux for 30 minutes after completion of the addition of IP. The reaction mixture was cooled to 80° C. and extracted three times with 50 ml of heptane. The combined heptane phases were evaporated under reduced pressure. A viscous oil was obtained. For the yield of (all-rac)-TCPA, based on IP, see table 2.

TABLE 2

Results of the reaction in γ-butyrolactone

| catalyst | relative amount of catalyst [mol %] | yield of PTMHQA [%]* | yield of TCPA [%] | yield of TCP [%] | yield of "phytadienes" [%] |
|---|---|---|---|---|---|
| AgOTf | 0.01 | 50.6 | 2.0 | 0 | 23.6 |
| Sc(OTf)$_3$ | 0.05 | 37.4 | 18.5 | 0.2 | 24.9 |
| Hf(OTf)$_4$ | 0.005 | 46.0 | 6.5 | 0 | 22.4 |
| Ga(OTf)$_3$ | 0.01 | 41.3 | 9.4 | 0 | 24.6 |

*minor amounts of isomers included

Example 3

In a four-necked flask equipped a with stirrer, a water separator, and a reflux condenser, 39.24 g (200 mmol) of TMHQA, 30 g of ethylene carbonate and 450 ml of heptane were heated with stirring under argon atmosphere to reflux (oil bath 140° C.). After the addition of the catalyst (for the relative amount of the catalyst, based on IP, see table 3), 36.18 ml (100 mmol) of IP were added at a rate of 0.8 ml per minute. The reaction mixture was heated for additional 10

TABLE 1

Results of the reaction in non-polar or polar solvents

| catalyst | relative amount of catalyst [mol %] | solvent | yield of TCPA [%] | yield of TCP [%] | yield of PTMHQA [%]* | yield of "phytadienes" [%]♦ |
|---|---|---|---|---|---|---|
| AgOTf | 0.01 | toluene | 55.4 | 0 | 11.1 | 24.1 |
| Sc(OTf)$_3$ | 0.05 | toluene | 64.6 | 0.2 | 6.2 | 22.9 |
| Hf(OTf)$_4$ | 0.005 | toluene | 47.8 | 0.2 | 19.4 | 26.1 |
| Ga(OTf)$_3$ | 0.01 | toluene | 71.6 | 0.8 | 0.1 | 20.8 |
| Hf(OTf)$_4$ | 0.005 | heptane | 54.1 | 0 | 19.6 | 20.1 |
| AgOTf | 0.01 | n-butyl acetate | 62.4 | 0.4 | 0.3 | 27.4 |
| Sc(OTf)$_3$ | 0.05 | n-butyl acetate | 53.8 | 0.3 | 7.7 | 30.2 |
| Hf(OTf)$_4$ | 0.005 | n-butyl acetate | 60.7 | 0.6 | 1.6 | 29.3 |
| Ga(OTf)$_3$ | 0.01 | n-butyl acetate | 59.2 | 1.2 | 0.8 | 31.0 |

*minor amounts of double bond isomers are included
♦"Phytadienes" are a mixture of several C-20 isomers formed by dehydration reactions of the starting material, the compound represented by formula III or IV, and can be removed in an easy way from the product, e.g. by distillation.

minutes, then the heptane was distilled off within approximately 20 minutes. Afterwards the reaction mixture was heated for the time indicated in table 3 at 80 to 90° C. The reaction mixture was cooled down to 80° C. 150 ml of heptane were added to the reaction mixture. The reaction mixture was stirred for additional 10 minutes at 80 to 90° C. The mechanical stirrer was removed and the reaction mixture was cooled to 5° C. The heptane layer was separated and evaporated under reduced pressure. A viscous oil was obtained. For the yield of (all-rac)-TCPA, based on IP, see table 3.

TABLE 3

Results of the reaction in a biphasic solvent system consisting of ethylene carbonate and heptane

| catalyst | amount of catalyst [mol %] | reaction time [minutes] after heptane was distilled off | yield of TCPA [%] | yield of PTMHQA [%]* | yield of TCP [%] | yield of "phytadienes" [%] |
|---|---|---|---|---|---|---|
| Sc(OTf)$_3$ | 0.0125 | 60 | 90.7 | 1.6 | 0.5 | 3.5 |
| Sc(OTf)$_3$ | 0.0125 | 75 | 92.1 | 0.6 | 0.6 | 3.3 |
| Sc(OTf)$_3$ | 0.05 | 25 | 92.3 | 0 | 2.5 | 3.2 |
| AgOTf | 0.01 | 25 | 87.0 | 6.1 | 0.3 | 3.9 |
| AgOTf | 0.01 | 60 | 93.0 | 0 | 2.1 | 2.5 |
| Hf(OTf)$_4$ | 0.005 | 60 | 93.3 | 0.2 | 1.4 | 3.0 |
| Ga(OTf)$_3$ | 0.01 | 25 | 92.2 | 0 | 2.1 | 3.2 |

*minor amounts of double bond isomers included

Example 4

In a four-necked flask equipped with a stirrer, a water separator, and a reflux condenser, 39.24 g (200 mmol) of TMHQA, 30 g of ethylene carbonate, and 450 ml of heptane were heated under argon atmosphere to reflux (oil bath 140° C.). After the addition of catalyst (for the relative amount of catalyst, based on IP, see table 4 below), 36.18 ml (100 mmol) of IP were added at a rate as indicated in table 4. Approximately 1.8 ml of water were separated after complete addition of IP. Afterwards the reaction mixture was heated for 10 minutes under reflux. The reaction mixture was cooled to 5° C. under stirring. The heptane layer was separated and evaporated under reduced pressure. A viscous oil was obtained. For the yield of (E,Z)-(all-rac)-PTMHQA (E:Z=2.2-2.4:1), based on IP, see table 4.

Example 5

In a 200-ml four-necked flask equipped with a mechanical stirrer, a thermometer, a water separator and a reflux condenser, 9.7 g (49.5 mmol) of TMHQA, 40 g of ethylene carbonate, the catalyst Gd(F$_3$CSO$_3$)$_3$ (for the relative amount of catalyst, based on IP, see table 5) and 50 ml of heptane were filled in. The reaction mixture was heated up under argon atmosphere to reflux (oil bath 140 to 145° C.). 11.9 ml (33 mmol) of IP were added at a rate of 0.6 ml per minute. Approximately 0.2 ml of water were collected after complete addition of IP. The heptane was distilled off within approximately 20 minutes. Afterwards the reaction mixture was heated for 22 hours at 125 to 130° C. The reaction mixture was cooled down to 80° C. 50 ml of heptane were added to the carbonate phase. The reaction mixture was stirred for additional 10 minutes at 50° C. The heptane layer was separated and evaporated under reduced pressure. A viscous oil was obtained and analysed by gas chromatography (GC) (using the internal standard consisting of 1.0 g squalene, 100 ml pyridine and 100 ml N,O-bis(trimethylsilyl)trifluoroacetamide (BSTFA)+1% trimethylchlorosilane (TMCS)). For the yield of (all-rac)-α-tocopheryl acetate, based on IP, see table 5.

TABLE 4

Results of the reaction in a biphasic solvent system consisting of ethylene carbonate and heptane

| Catalyst | amount of catalyst [mol %] | rate of addition of IP [ml/minute] | yield of PTMHQA [%]* | yield of TCPA [%] | yield of TCP [%] | yield of "phytadienes" [%] | yield of IP [%] |
|---|---|---|---|---|---|---|---|
| Sc(OTf)$_3$ | 0.05 | 0.8 | 55.6 | 33.4 | 1.3 | 6.4 | 0 |
| Sc(OTf)$_3$ | 0.01 | 0.8 | 72.5 | 1.9 | 0 | 4.8 | 12.1 |
| Sc(OTf)$_3$ | 0.01 | 0.4 | 85.9 | 2.6 | 0 | 5.7 | 0 |
| Ga(OTf)$_3$ | 0.0075 | 0.8 | 69.0 | 20.2 | 0.4 | 5.9 | 0 |

*minor amounts of double bond isomers included

TABLE 5

Results of the reaction in the presence of Gd(OTf)₃ as catalyst

| relative amount of Gd(OTf)₃ [mol %] | reaction time [hours] | yield of TCPA [%] | yield of PTMHQA [%]* | yield of TCP [%] | yield of "phytadienes" [%] |
|---|---|---|---|---|---|
| 2 | 22 | 61.4 | 11.7 | 0.4 | 6.4 |
| 1 | 22 | 62.4 | 12.9 | 0.4 | 6.0 |
| 0.5 | 17 | 64.3 | 11.1 | 0.5 | 7.4 |
| 0.2 | 20 | 35.2 | 40.2 | 0.0 | 7.0 |

*minor amounts of double bond isomers included

Example 6

1.00 mmol of (E/Z)-(all-rac)-PTMHQA was transferred to a Schlenk tube under argon and dissolved in 3 ml of n-butyl acetate or 3 ml of γ-butyrolactone or 3 ml of toluene or 1.2 g of ethylene carbonate. The solution was heated up to 130 to 140° C. (oil bath temperature) and 25 µl (0.05 mol %, based on PTMHQA) or 12.5 µl (0.025 mol %, based on PTMHQA) of a stock solution of the catalyst in water (for Sc(OTf)₃ 0.2 molar; Ga(OTf)₃ 0.2 molar; AgOTf 0.2 molar; Hf(OTf)₄ 0.2 molar) were added. The reaction mixture was heated for one hour. Then the solution was cooled to room temperature and the solvent removed under reduced pressure (in the case of using toluene or n-butyl acetate as solvent). In the case of using γ-butyrolactone as solvent the reaction mixture was extracted three times with approximately 5 ml of heptane. In the case of using ethylene carbonate as solvent, 5 ml of heptane were added to the reaction mixture, the mixture was cooled down to 5° C., the layers were separated, and the heptane phase was concentrated in vacuo. The obtained oils were examined by gas chromatography (GC) analysis. For the yields, based on PTMHQA, see table 6.

acetate with a compound selected from the group consisting of phytol (formula IV with R=OH), isophytol (formula III with R=OH), and (iso)phytol derivatives represented by the following formulae III and IV with R=C₂₋₅-alkanoyloxy, benzoyloxy, mesyloxy, benzenesulfonyloxy or tosyloxy,

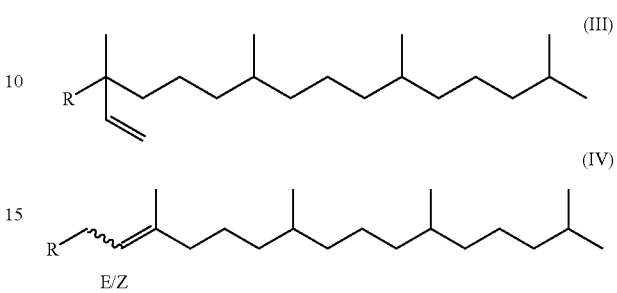

in the presence of a catalyst of the formula $M^{n+}(R^1SO_3^-)_n$, wherein $M^{n+}$ is a silver, copper, gallium, hafnium or rare earth metal cation, n is the valence of the cation $M^{n+}$ and $R^1$ is fluorine, perfluorinated $C_{1-8}$-alkyl or perfluorinated aryl, and, if required, cyclizing any 3-phytyl-2,5,6-trimethylhydroquinone-1-acetate or a double bond isomer thereof obtained as an intermediate reaction product, to produce α-tocopheryl acetate.

2. The process as in claim 1, wherein in the catalyst $M^{n+}$ is $Ag^+$, $Cu^+$, $Ga^{3+}$, $Sc^{3+}$, $Lu^{3+}$, $Ho^{3+}$, $Tm^{3+}$, $Yb^{3+}$ or $Hf^{4+}$.

3. The process as in claim 1, wherein in the catalyst $M^{n+}$ is $Ag^+$, $Ga^{3+}$, $Sc^{3+}$ or $Hf^{4+}$.

4. The process as in claim 1, wherein in the catalyst R' is trifluoromethyl.

5. The process as in claim 1, wherein the catalyst is used in a relative amount of from about 0.001 mol % to about 1 mol %, based on 2,3,6-trimethyl-hydroquinone-1-acetate or a compound represented by formula III or IV, whichever is used in the lesser molar amount.

TABLE 6

Results of the cyclization of PTMHQA to TCPA

| catalyst | amount of catalyst [mol %] | oil bath temperature [° C.] | solvent | yield of TCPA [%] | yield of TCP [%] | yield of PTMHQA [%]* | yield of "phytadienes" [%] |
|---|---|---|---|---|---|---|---|
| Sc(OTf)₃ | 0.05 | 130 | ethylene carbonate | 94.9 | 0.1 | 6.0 | 0.9 |
| Sc(OTf)₃ | 0.05 | 140 | ethylene carbonate | 99.4 | 1.3 | 0.1 | 0.9 |
| Sc(OTf)₃ | 0.05 | 130 | γ-butyrolactone | 100.7 | 1.0 | 0.1 | 1.2 |
| Sc(OTf)₃ | 0.05 | 130 | n-butyl acetate | 5.7 | 0 | 85.8 | 4.7 |
| Sc(OTf)₃ | 0.05 | 130 | toluene | 39.0 | 0 | 63.5 | 1.0 |
| AgOTf | 0.05 | 140 | ethylene carbonate | 94.8 | 0.3 | 6.0 | 0.9 |
| Ga(OTf)₃ | 0.025 | 140 | γ-butyrolactone | 98.9 | 3 | 0 | 0.9 |
| Hf(OTf)₄ | 0.025 | 140 | γ-butyrolactone | 97.6 | 0.7 | 0.7 | 1.6 |

*minor amounts of double bond isomers included

The invention claimed is:

1. A process for the manufacture of α-tocopheryl acetate which comprises reacting 2,3,6-trimethylhydroquinone-1-

6. The process as in claim 1, wherein 2,3,6-trimethylhydroquinone-1-acetate is reacted with phytol and/or isophytol, preferably with phytol, and, if required, any 3-phytyl- 2,5,6-trimethylhydroquinone-1-acetate or a double bond isomer thereof obtained as an intermediate reaction product is cyclized, to produce α-tocopheryl acetate.

7. The process as in claim 1, wherein the process is carried out in an aprotic non-polar or an aprotic polar organic solvent.

8. The process as in claim 1, wherein the process is carried out in a biphasic solvent system of a polar solvent and a non-polar solvent.

9. The process as in claim 8, wherein the polar solvent is selected from the group consisting of aliphatic and cyclic carbonates, aliphatic esters and cyclic esters, aliphatic and cyclic ketones, and mixtures thereof, and the non-polar solvent is selected from the group consisting of aliphatic hydrocarbons and aromatic hydrocarbons.

10. The process as in claim 9, wherein the polar solvent is at least a cyclic carbonate, and the non-polar solvent is at least a linear, branched or cyclic $C_5$- to $C_{15}$-alkane.

11. The process as in claim 10, wherein the polar solvent is ethylene carbonate or propylene carbonate or a mixture thereof, preferably ethylene carbonate, and the non-polar solvent is hexane, heptane, octane, cyclohexane or methylcyclohexane or a mixture thereof, preferably heptane.

12. The process as in claim 7, wherein from about 0.25 ml to about 6 ml, preferably from about 0.5 ml to about 3 ml, of an organic solvent are used per mmol of the compound represented by formula III or IV, whichever is employed, these amounts referring to the total amount of solvent, i.e. regardless of whether the reaction is effected in a single phase (non-polar organic solvent or polar organic solvent) or in a biphasic solvent system (non-polar organic solvent and polar organic solvent).

13. The process as in claim 8, wherein the volume ratio of the non-polar solvent to the polar solvent in the biphasic solvent system is in the range from about 1:5 to about 30:1, preferably from about 1:3 to about 20:1, especially from about 10:1 to about 15:1.

14. The process as in claim 1, wherein the molar ratio of 2,3,6-trimethylhydroquinone-1-acetate to the compound represented by formula III or IV present in the reaction mixture is from about 3:1 to about 0.8:1, preferably from about 2:1 to about 1:1, more preferably from about 1.75:1 to about 1:1.

15. The process as in claim 1, wherein the reaction is carried out at temperatures from about 20° C. to about 160° C., preferably from about 80° C. to about 150° C., especially from about 105° C. to about 150° C., most preferably from about 125° C. to about 145° C.

16. The process as in claim 1, wherein 2,3,6-trimethylhydroquinone-1-acetate is reacted with isophytol or phytol in the presence of a catalyst of the formula $M^{n+}(R^1SO_3^-)_n$, wherein $M^{n+}$ is a silver, copper, gallium, hafnium or rare earth metal cation, n is the valence of the cation $M^{n+}$ and $R^1$ is fluorine, $C_{1-18}$-perfluoroalkyl or perfluoroaryl, in an aprotic organic solvent, and, if required, any 3-phytyl-2,5,6-trimethylhydroquinone-1-acetate or a double bond isomer thereof obtained as an intermediate reaction product is cyclized to produce α-tocopheryl acetate.

\* \* \* \* \*